US008342136B2

United States Patent
Hadjioannou et al.

(10) Patent No.: US 8,342,136 B2
(45) Date of Patent: Jan. 1, 2013

(54) METHOD AND APPARATUS FOR ANIMAL POSITIONING IN IMAGING SYSTEMS

(75) Inventors: Arion-Xenofon Hadjioannou, Los Angeles, CA (US); David B. Stout, Culver City, CA (US); Robert W. Silverman, Sherman Oaks, CA (US)

(73) Assignee: The Regents of the University of California, Oakland, CA (US)

( * ) Notice: Subject to any disclaimer, the term of this patent is extended or adjusted under 35 U.S.C. 154(b) by 1100 days.

(21) Appl. No.: 11/660,298

(22) PCT Filed: Aug. 12, 2005

(86) PCT No.: PCT/US2005/028792
§ 371 (c)(1),
(2), (4) Date: Jun. 20, 2008

(87) PCT Pub. No.: WO2006/020896
PCT Pub. Date: Feb. 23, 2006

(65) Prior Publication Data
US 2009/0000567 A1    Jan. 1, 2009

Related U.S. Application Data

(60) Provisional application No. 60/601,333, filed on Aug. 13, 2004.

(51) Int. Cl.
*A01K 15/04*    (2006.01)
(52) U.S. Cl. ............ 119/755; 118/756; 5/601; 378/174
(58) Field of Classification Search ............ 5/601, 603, 5/629, 722, 723; 119/755, 756; 250/362; 378/174, 180; 128/200.11–202.84
See application file for complete search history.

(56) References Cited

U.S. PATENT DOCUMENTS

| | | | | |
|---|---|---|---|---|
| 3,040,174 A | * | 6/1962 | Robin | 5/621 |
| 4,184,451 A | | 1/1980 | Carlin | |
| 4,911,106 A | | 3/1990 | Goodwin | |
| 5,324,911 A | | 6/1994 | Cranston et al. | |
| 5,385,119 A | | 1/1995 | Tarulli | |
| 5,462,050 A | * | 10/1995 | Dahlstrand | 128/207.18 |
| 5,525,905 A | | 6/1996 | Mohapatra et al. | |
| 5,992,416 A | | 11/1999 | Jackson, Sr. | |
| 6,488,029 B1 | * | 12/2002 | Hood et al. | 128/845 |
| 6,782,571 B1 | | 8/2004 | Josephson et al. | |
| 7,255,671 B2 | * | 8/2007 | Boone et al. | 600/22 |

* cited by examiner

*Primary Examiner* — Robert G Santos
*Assistant Examiner* — Brittany Wilson
(74) *Attorney, Agent, or Firm* — Christie, Parker & Hale, LLP

(57) ABSTRACT

An apparatus for imaging an animal includes a first mounting surface, a bed sized to support the animal and releasably secured to or integral with the first mounting surface. The apparatus also includes a plurality of straps, each having a first end in a fixed position relative to the bed and a second end for tightening around a limb of the animal. A method for in-vivo imaging of an animal includes providing an animal that has limbs, providing a first mounting surface, and providing a bed removably secured to or integral with the mounting surface and sized to support the animal as well as being coupled to a plurality of straps. The method also includes placing the animal on the bed between the plurality of straps and tightening at least two of the plurality of straps around at least two of the limbs such that the animal is substantially secured in place relative to the bed.

4 Claims, 5 Drawing Sheets

METHOD AND APPARATUS FOR ANIMAL POSITIONING IN IMAGING SYSTEMS

ACKNOWLEDGEMENT OF GOVERNMENT SUPPORT

This invention was made with Government support of Grant No. R24 CA 92865, awarded by the National Institute of Health, and DE-FC03-02ER63420, awarded by the Department of Energy. The Government has certain rights in the invention.

FIELD OF THE INVENTION

The present invention relates to in-vivo animal imaging, namely a method and apparatus for positioning and imaging small animals for in-vivo imaging.

BACKGROUND OF THE INVENTION

In-vivo imaging of small animals to investigate biological functions, particularly those related to cancer, has become commonplace in the past few years. The advent of imaging systems such as the Concorde MicroPET, MicroSPECT, ImTek MicroCAT, MR, Xenogen IVIS optical imaging systems, and others specifically designed to image small animals, has resulted in a substantial increase in research of animal models of disease. Currently, each of these systems is designed and built independently. As such, each manufacturer has built its own stage for mounting animals or animal holders to its imaging system. Hence, there is currently no common platform for imaging animals in multiple systems without moving the animals to separate, proprietary stages.

One of the main strengths of in-vivo imaging is the ability to image the same animal repeatedly over time or in different imaging devices and accurately compare the images. When an animal is used only for a single data point in a test, trends over time become more difficult to detect, as there are frequently individual differences between the animal subjects. Thus, substantially more data must be collected. Testing a single animal multiple times would thus increase the ease and efficiency of such testing. Data analysis of the resulting images is aided by reproducibly positioning the animal, such that the orientation is consistent across all the images. Current positioning systems, such as taping an animal in place or holding its head with toothbars and ear plugs, do not adequately provide such reproducible positioning of the animal's body.

Positioning is also important in certain imaging systems to ensure that all of the animal is contained within a particular space, and that the animal is centered within the field of view. Some imaging devices, such as CT, are subject to considerable artifacts in the resulting images if any part of the animal extends outside the field of view.

Combined or fused images are images formed by merging several images of the same subject taken at different times or using multiple imaging systems. Such fused images can be very beneficial for a researcher to review multiple biological structures, which may be visible in one imaging method but not another or for viewing changes in an animal over time. Alignment of the images when using multiple imaging systems is essential, therefore the animal must be held immobile during the entire imaging process.

To compare separate images over time or to create fused images, data acquired from an image is typically measured in a device-specific coordinate system, which must be translated to a common coordinate system to compare with data from other imaging devices or sessions. This procedure is called "registration." Accurate registration depends on knowledge of both orientation of the subject and its location within the imaging system. Since three dimensional objects, such as small animals, can be placed inside an imaging device in innumerable orientations, registration presents a difficult problem.

Several types of registration are known in the art. Software registration employs software to track and correlate either landmarks on the subject or redundant data detected in the subject, such as an eye. External markers called fiducials fixed on the animal can also be used. These markers, however, may move relative to animals and create inaccuracies in the software image registration. Software registration is also limited in that only small changes in orientation can be corrected for. Software registration can be expensive, inaccurate, and time consuming, but is frequently used in small animal imaging for lack of an effective alternative. Additionally, there may be insufficient data available in one or more images for software methods to properly operate, as in the case when only a spherical tumor and nothing else is visible.

Hardware registration, such as tracking the location of fiducial marker on hardware relative to the location of the animal is also used in some systems. The relative positioning of the fiducial to the animal, however, cannot typically be determined with sufficient accuracy when the orientation of the subject is changed slightly between sessions or devices, so hardware registration is typically not possible with multiple imaging sessions in small animals.

Another problem with current imaging systems is that animals are exposed to pathogens. Research using small animals has increasingly utilized various types of transgenic and immuno-compromised animal models. Currently, the imaging systems used with these animals do not offer any type of pathogen barrier to shield the animals from pathogens in the open air.

In-vivo imaging of live animals usually requires that the animals remain motionless during the image acquisition process. For most imaging experiments using small animals, this requires the animal to remain stationary for 10-60 minutes. Safe levels of injected anesthetics typically last only 30-50 minutes, and may not be suitable for longer experiments, or for experiments where two or more imaging systems are used to image the animal and exactly the same positioning is desired. Injected anesthetics also suffer from a variable depth of anesthesia over time, which may affect the biological processes under investigation.

The use of gas anesthetics has become common. Gas provides a constant, easily controlled depth of anesthesia and offers essentially indefinite duration for longer experiments. The use of gas anesthesia is also safer for the animals since it is unlikely the animal will receive an overdose of anesthetic. Recovery times are also very short for gas compared to injected anesthetics, which reduces stress and the amount of time spent in an altered physiological condition. This is particularly important for imaging research where the same animal is frequently imaged, perhaps as often as once per day.

To keep animals alive and healthy for imaging experiments where anesthesia lasts more than a few minutes, it is necessary to keep the animals warm to prevent hypothermia. Without heating, the effects of hypothermia will result in physiological stress or even death to the animals, which is likely to adversely effect uptake and metabolism of injected compounds used for examining biological functions or disease processes. Hypothermia-induced changes are typically not desirable. Therefore, animals are preferably maintained at or near normal physiological temperatures during imaging experiments.

Currently, few systems offer any heating options, and there is not an integrated system available to ensure the animals are kept at normal physiological temperatures throughout the whole imaging experiment process. For microPET research, this is particularly important, since there is often a period of uptake after an imaging agent is injected and prior to image acquisition. If the animal is cold and peripheral blood supply is restricted to maintain core body temperature, there may be little or no uptake into subcutaneous tumors, thus compromising the intended investigation. One option used by some is heating of the air or gas anesthesia. However, this method delivers little heat, due to the low heat capacity of gasses, and when used for extended times can lead to dehydration of the animals.

The creation of disease models in small animals is often a time consuming and expensive process. The complex nature of creating these animal disease models often requires weeks or months of preparation and analysis. Considerable investment in time and money is often spent to create and image these animals. Therefore, the loss of even a single animal can be quite substantial. There is a definite need for equipment and procedures that will aid the collection of imaging data and ensure the health of the animals. In addition, there is a need for ease of use to facilitate high throughput animal imaging to make the most efficient use of time and resources.

SUMMARY OF THE INVENTION

To address one or more of the needs discussed above, an apparatus and method of in-vivo imaging of an animal is provided. An animal is placed on a bed that is sized to support the animal and held in place with straps coupled to the bed. The bed is removably secured to or integral with a first mounting surface. In this embodiment, the straps are tightened around at least two of the animal's limbs such that the animal is substantially secured in place relative to the bed.

In a further embodiment, the first mounting surface is fixed to a second mounting surface associated with a first imaging device. The bed and animal are located within a field of view of the first imaging device and the animal is imaged to create a first image.

In another embodiment, the bed is enclosed in a chamber and is environmentally isolated from the second mounting surface. Another embodiment of the method also includes separating the first and second mounting surfaces, fixing the first mounting surface to a third mounting surface associated with a second imaging device, locating the animal within a field of view of the second imaging device, and imaging the animal with the second imaging device to create a second image. Alternatively, the animal is removed from the bed after imaging, and the above steps are repeated to take a second image of the animal in the first imaging device. In a further embodiment, the first and second images from either the first imaging device or the first and second imaging devices are fused into a third image.

Another embodiment of the system and method of the invention includes providing gas anesthesia through a mouthpiece. An air exhaust chamber may also be added to capture the air exiting from the chamber. The animal can also be heated through a heating element in the bed. In one embodiment of the apparatus, a cover encloses the bed to form an air sealed chamber.

In one embodiment, the bed is curved. In yet another embodiment, the apparatus includes at least two posts projecting through openings in the bed and fixed to a supporting surface supporting the bed. The posts have circumferential grooves in one embodiment that receive the straps. The posts may also have a clamp at a distal end to fix the straps to the posts. The straps can then be tied or tightened around at least two of the animal's limbs.

DETAILED DESCRIPTION OF THE PREFERRED EMBODIMENTS

Figure 1:
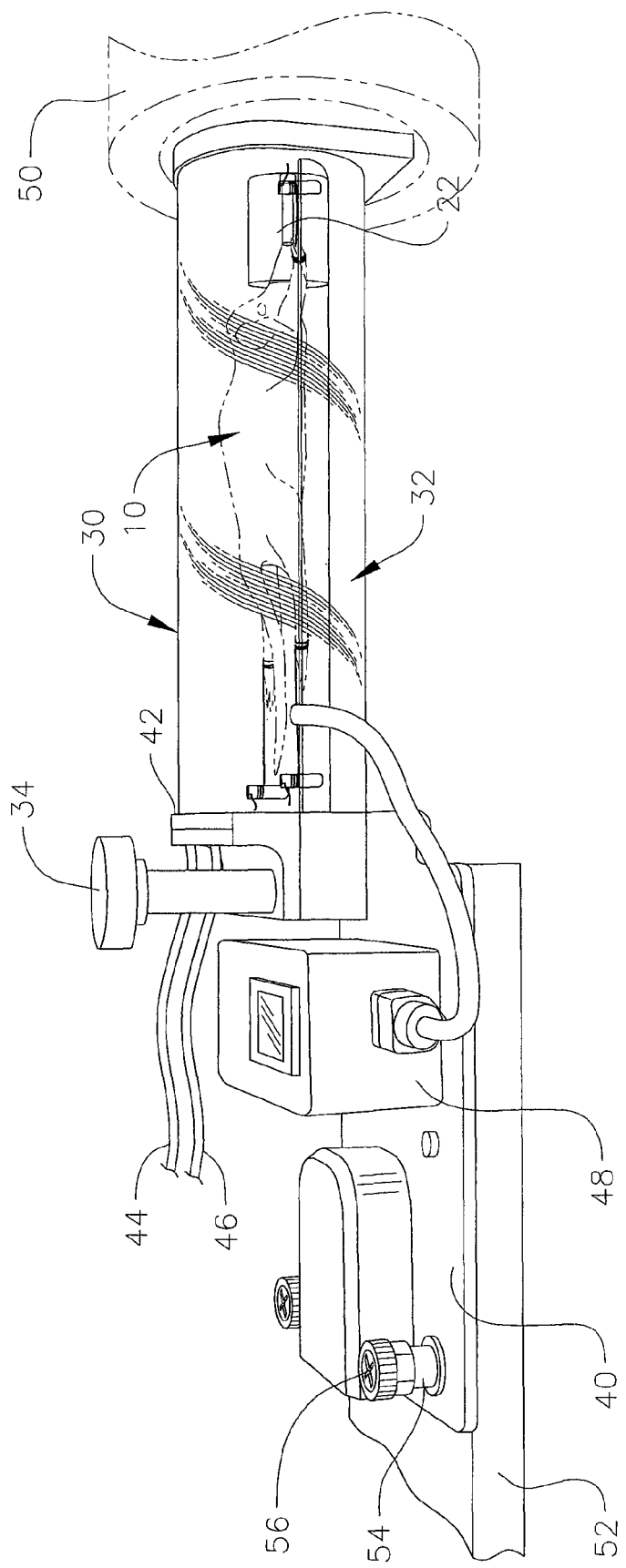
FIG. 1 is a side perspective view of an apparatus according to one embodiment of the invention.
Figure 2:
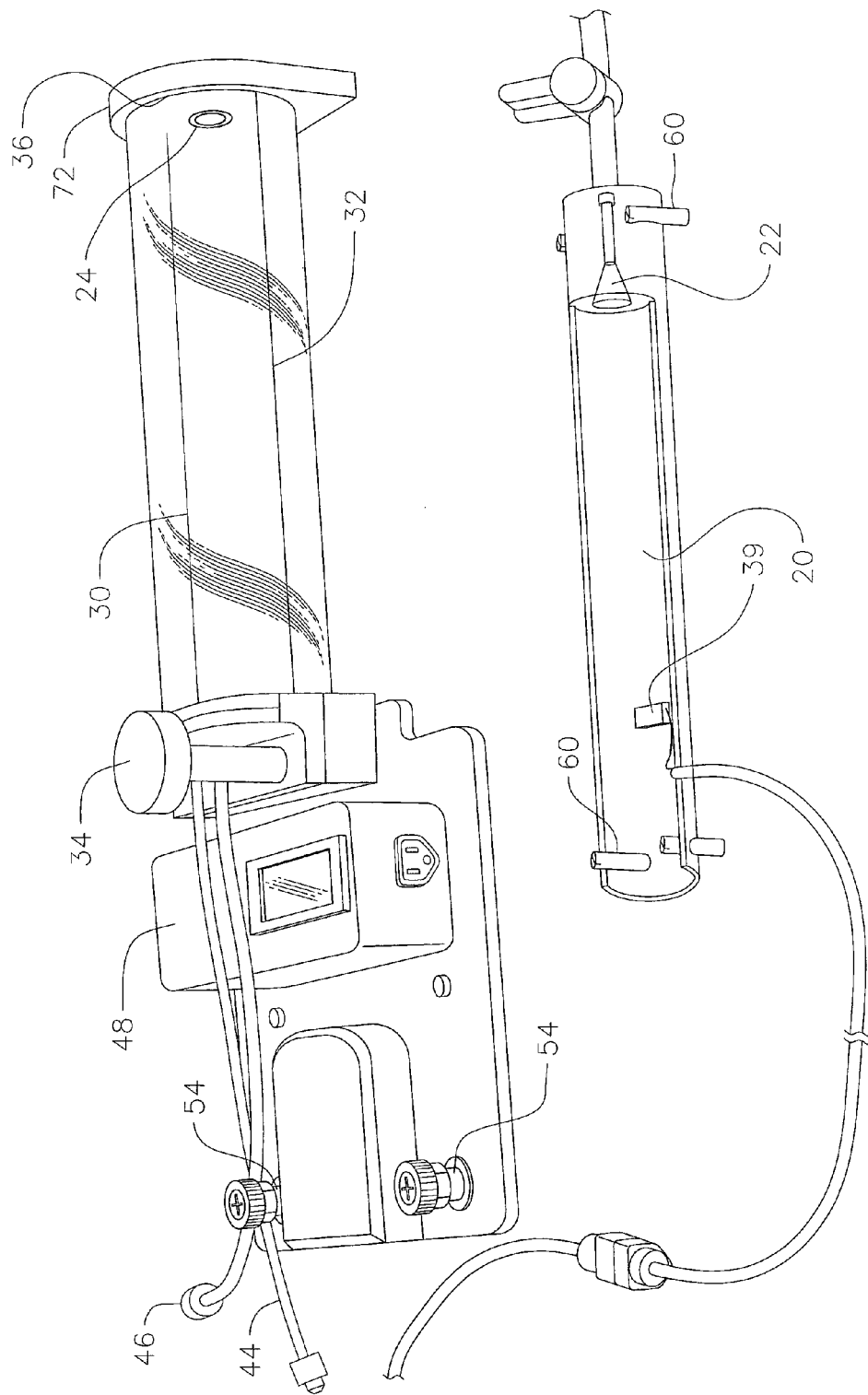
FIG. 2 is an elevated perspective view of an unassembled chamber, bed and mounting plate shown in FIG. 1.
Figure 3:
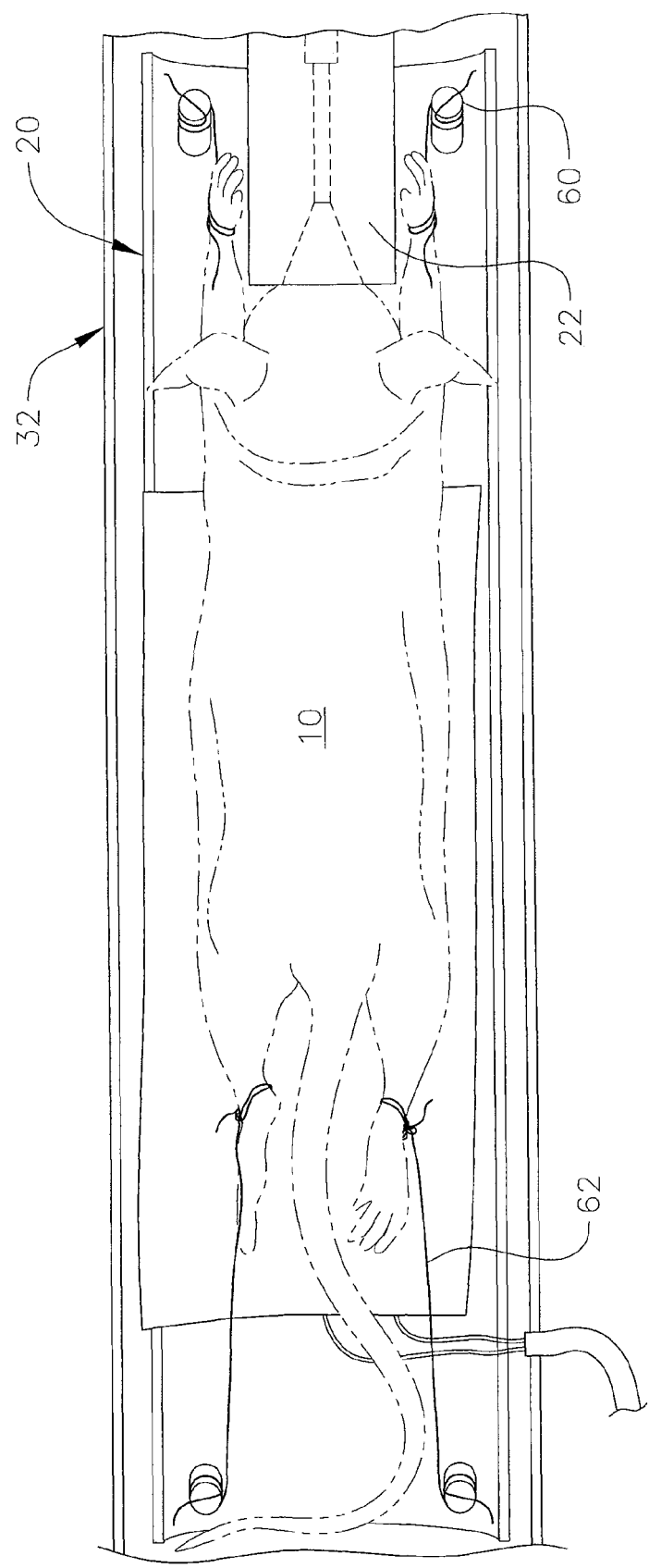
FIG. 3 is a plan view of the chamber and bed of the embodiment shown in FIGS. 1 and 2.
Figure 5:
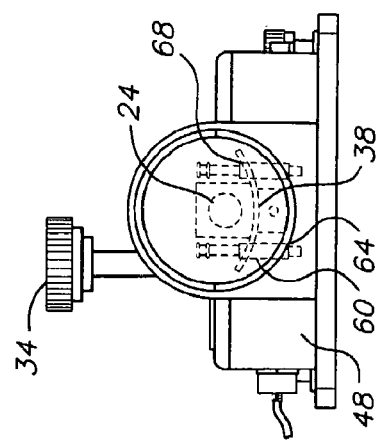
FIG. 5 is an end view of the embodiment shown in FIG. 4.
Figure 4:
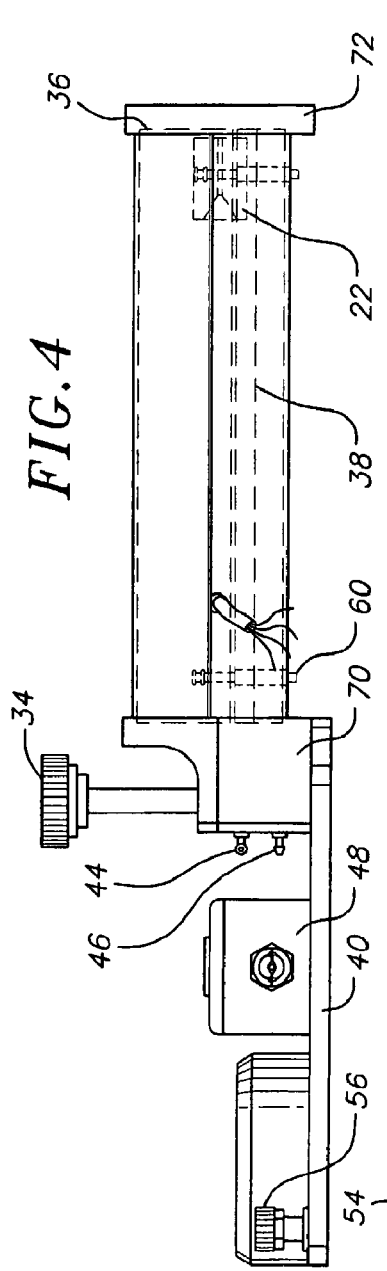
FIG. 4 is a side diagrammatic view of the embodiment shown in FIGS. 1-3.
Figure 6:
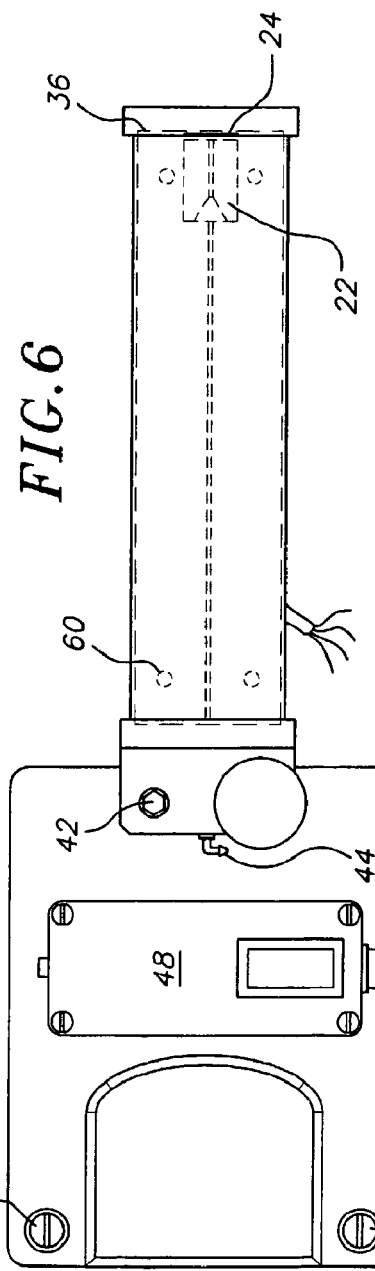
FIG. 6 is a plan view of the embodiment shown in FIG. 4.
Figure 7:
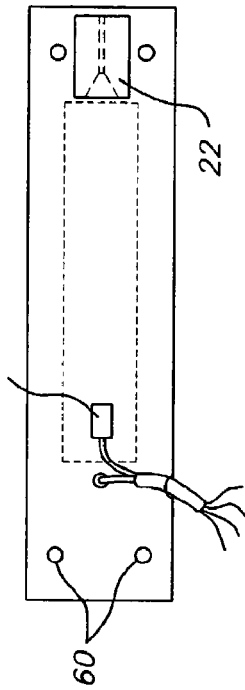
FIG. 7 is a bottom view of the embodiment shown in FIG. 4.

One embodiment of an apparatus for imaging an animal is shown in FIG. 1. An animal 10 is supported on a bed 20 that sits within a chamber 30, 32. In this embodiment, both the chamber and the bed are acrylic, but it is within the scope of the invention to construct the chamber and bed out of any material suitable for housing and supporting the animal for imaging within the particular imaging device.

The chamber 30, 32 is fixed to a first mounting surface 40 that also includes an anesthetic delivery system 42 and a heating element control 48. The first mounting surface 40 is fixed to a second mounting surface 52 associated with a first imaging device 50. In this embodiment, the first mounting surface 40 is a metallic plate coupled to one edge of the chamber 30, 32, but it is also within the scope of the invention for the first mounting surface 40 to be any other material compatible with the imaging device 50 or a mountable surface of the bed 20 or chamber 30 itself that will provide durable, accurate positioning.

In the embodiment shown in FIGS. 1-9, the first mounting surface 40 is attached to the second mounting surface 52 via two metal pins 54 and a capture screw 56 to firmly affix the surfaces 40, 52 together.

The chamber 30, 32 is attached to the first mounting surface 40 using a single recessed screw 42 and two alignment pins (not shown). The first mounting surface 40 and chamber 30, 32, however, can be fixed together using any suitable means that will hold the chamber 30, 32 firmly in place relative to the second mounting surface 52.

In this embodiment, only the mounting surfaces 40, 52 are separated between uses, with the chamber 30, 32 and the first mounting surface 40 left together. The first mounting surface 40 is further adapted in this embodiment to easily secure to a third mounting surface (not shown) on a second imaging device (not shown). This adaptation allows the apparatus to be easily moved from one imaging system to another with little or no alteration of the apparatus or positioning of the animal within it, increasing the ease and uniformity of positioning.

The chamber 30, 32 in the embodiment shown positions the animal 10 in the center of the imaging field of view, maintains a pathogen barrier, supplies anesthetic gas, and keeps the animal 10 at a constant temperature. The chamber 30, 32 is of a split design for easy access to the internal, curved acrylic bed 20 holding the subject 10, with the upper and lower halves 30, 32 held together by a machined groove 36 on the endplate 72 and a single thumbscrew 34 at the rear. However, one skilled in the art will understand that the upper and lower halves 30, 32 may be held together by any suitable means.

Inside the chamber 30, 32 is a curved bed 20, which has a resistive wire heating element 38 attached to its under side, a platinum resistance temperature sensor 39 at the rear of the upper side, and four notched posts 60 extending above the corners to serve as tie-points for securing the animal subject 10. Also on the bed 20 is a nose cone or mouthpiece 22 for delivery of gas anesthesia.

Tubes 44, 46 connected to the rear portion of the chamber 30, 32 allow for entry of gas anesthetic through the nose cone 22 at the front of the bed 20 and for the removal of gasses from inside the enclosed chamber 30, 32. The chamber 30, 32 in this embodiment is constructed from materials allowing it to be effectively used with positron emission tomography (PET) and x-ray computed tomography (CT) imaging modalities, and is built to hold an average-size mouse. It is within the scope of the invention, however, to construct the chamber 30, 32 from any size and material suitable for the particular animal and imaging device being used. Factors that may determine the suitability are, for example, transparency to the imaging device, durability, rigidity, structural integrity, etc.

Suture thread is used as straps 62 to tie the limbs of the animal 10 in place. However, any suitable material, such as paper tape, thread, etc., able to be tightened securely around limbs of the animal 10 can be substituted. The straps 62 are fixed to the posts 60 to maintain a fixed position of the subject 10 in the imaging system 50 field of view. These four posts 60 extend below the bed 20 and fit into holes 64 in the chamber 30, 32 to secure the bed 20 inside of the chamber 30, 32. Alternatively, the posts 60 can be fixed directly to the bed 20 and/or lower half 30 of the chamber 30, 32.

Figure 8:
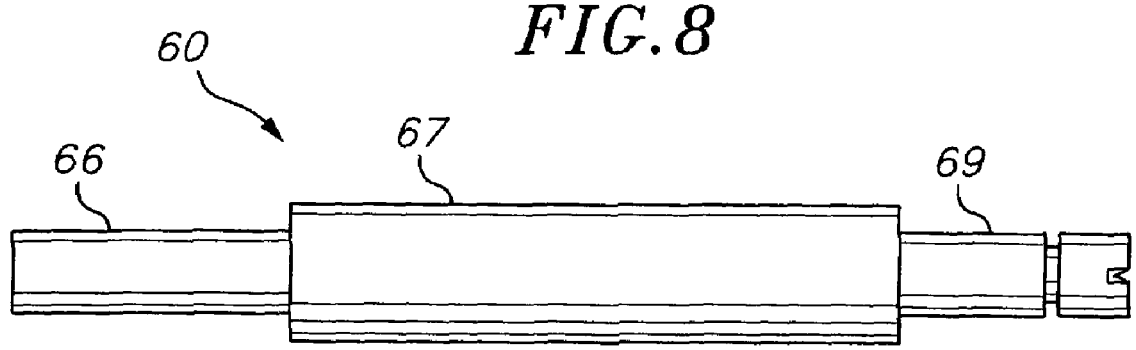
FIG. 8 is a side perspective view of one embodiment of a post according to the invention.
Figure 9:
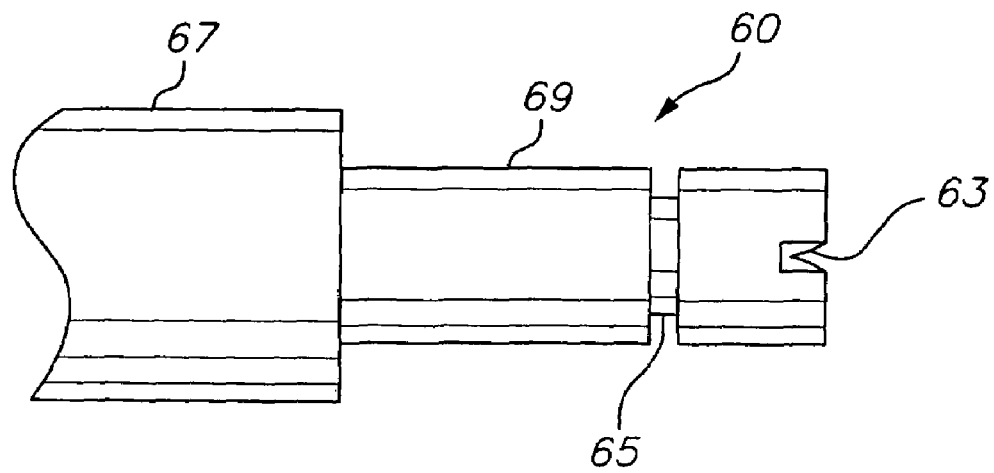
FIG. 9 is a detailed perspective view of the post shown in FIG. 8.

One embodiment of a post 60 is shown in more detail in FIGS. 8 and 9. The post 60 has a lower end 66 that is insertable into openings 68, 64 in the lower half of the chamber 30 and the bed 20, respectively (shown in FIGS. 1 and 5). The center portion 67 of the post 60 has a larger diameter than the lower 66 and upper 69 ends. The upper end 69 includes a circumferential ridge 65 around which the straps 62 can be tightened. A clamp 63 at the upper end 69 of the post 60 can receive an end of the strap 62 to fix it in place relative to the post 60.

In a further embodiment, the posts 60 can be replaced by openings (not shown) in the corners of the bed 20 through which the straps 62 can engage.

Referring again to FIGS. 2 and 3, the bed 20 provides gas anesthesia from underneath the animal 10 to allow the lower half of the chamber 30 to be used without the upper half 32, if so desired. Alternatively, the bed 20 itself can make up the lower half 30 of the chamber. In a further embodiment (not shown), the upper half of the chamber 32 is flat, as may be useful, for example, in optical imaging systems.

The chamber endplates 70, 72 contain grooves 36 that receive the two halves of the chamber 30, 32 to form a nearly gas tight connection.

A small O-ring 24 is located within grooves near the center of one of the endplates 72 of the chamber 30, 32 to seal off an opening from a Luer fitting in the nose cone 22 that ensures that the gas flows to the nose of the animal 10. The O-ring 24 also places a small amount of force against the nose cone 22, which pushes the bed 20 against the back 70 of the chamber 30, 32. The bed 20 can thereby be fixed in location relative to the chamber 30, 32 and the first mounting surface 40 in a reproducible manner.

The temperature of the animal 20 can also be controlled in this embodiment during imaging. A thin, electrical heating element 38 is attached to the bottom of the bed 20 that holds the animal 10. A temperature sensor 39 senses the temperature of the bed and sends this information to the electronics 48. The electronics 48 control the heater 38 using active feedback to maintain the set temperature. To avoid overheating the animal 10, risking death, both a minimum and maximum value of the heater 38 temperature can be set.

In one embodiment, heat is applied to the underside of the bed 20 to prevent anesthetic-induced hypothermia in the animal 10. A 19.1×101.6 mm sheet of clear polyester with an embedded, nickel-wire heating element 38, such as Model H6701, available from Minco Products, Inc, Minneapolis, Minn., is attached by means of an acrylic pressure-sensitive adhesive. Due to the small diameter of the nickel wire (0.03 mm), minimal artifacts are introduced into any of the imaging modalities used during preliminary testing.

Heater power is supplied through a miniature, on/off controller 48 such as the Minco CT325. The temperature can be monitored using a 5×12 mm, thin-ribbon, platinum resistance temperature detector 39 (Minco S665) attached to the upper, rear surface of the bed 20 over the heater 38 and connected to the controller 48. This location places the sensor 39 outside of the imaging field. The electronics 48 for providing on-off control of the heating element 38 and to monitor the temperature, in this embodiment, are contained in a small, aluminum box mounted on the first mounting surface.

In one embodiment of a method according to the invention, the animal 10 is placed on the bed 20 and its four limbs are tied with the straps 62. The tension in the straps 62 is adjusted to substantially secure the animal 10 from movement without harming it or interfering with blood flow. The nose cone 22 is placed around the nose of the animal 10. The top half of the chamber 32 encloses the animal 10 in its assembled state.

Once assembled, the chamber 30, 32 can then be carried to the desired imaging system 50 and attached to the second mounting surface 52. The first mounting surface 40 in this embodiment is aligned using two positioning pins 54 and held in place via a screw 56 designed for easy tightening by hand. Electrical power lines to the bed heater 38 and anesthesia delivery 46 and exhaust 44 tubing are then attached, and the chamber 30, 32 is ready for imaging.

The first mounting surface 40 is fixed to the second mounting surface 52 and the second mounting surface 52 is moved to bring the animal 10 within the field of view of the imaging device 50. The imaging device 50 can then take one or a series of images of the animal 10.

After the images are taken by the imaging device 50, the first mounting surface 40 can be removed from the second mounting surface 52, and the chamber 30, 32, bed 20, animal 10, and first mounting surface 40 can be moved to a second imaging device (not shown). The first mounting surface 40 can then be fixed to a third mounting surface (not shown) associated with this second imaging device. An image taken with the second imaging device can then be co-registered through hardware registration with the first image. Creation of a third, fused image can also be accomplished through such effective co-registration.

The apparatus and method described above is well suited for imaging of small animals such as mice and rats. In addition, the chamber 30, 32 described above can be well suited for a range of different imaging devices, including microPET, microSPECT, microCAT, small animal MRI, and optical systems.

The embodiment described above also provides a reproducible method for positioning small animals used in imaging research. Through the use of tie-down posts 60 and light tension using suture thread 62, animals can be quickly positioned on a bed 20 and enclosed in a chamber 30, 32. Initial studies have shown that this embodiment of the chamber 30, 32 provides reproducible animal positioning for longitudinal studies with an average location difference of 790 micrometers. The anesthesia nose cone 22 on the bed 20 is designed to easily attach a Luer fitting from the tubing 46 delivering gas anesthesia. This allows the investigator as much time as needed to secure and position the animal 10 without concerns for the animal regaining consciousness.

The bed 20 in this embodiment warms up quickly due to low thermal mass, and can also be preheated if desired. The bed 20 is curved to facilitate the reproducible positioning and to reduce the width of the animal 10. By avoiding a flat platform, the animal 10 is in a more natural position and has a smaller horizontal cross section and therefore more uniform attenuation and potentially better imaging characteristics. This chamber 30, 32 and bed 20 thus contain the animal 10 within a certain space and hold the animal in the optimal position for the imaging device (typically the center of the imaging area). However, it is also within the scope of the invention to provide a flat bed, which may provide more effective optical imaging.

The apparatus described above provides a stable platform for imaging in multiple systems without moving the animal relative to the apparatus, thus providing a fixed orientation of the animal for all the imaging modalities.

Software image registration is a computationally demanding and difficult problem to solve, one that can be avoided or simplified using the chamber 30, 32. With the chamber 30, 32, often only a fixed offset is needed to align the images from different systems. Initial testing has shown that the movements in positioning when changing the chamber 30, 32 from one imaging device to another are minimal, ~82 microns, and well below the resolution of current microPET systems. Thus, images can be registered using only hardware registration.

The use of gas anesthesia and heating of the animal 10 to maintain normal physiology can reduce movement artifacts and effects of hypothermia. This can be particularly advantageous for longer experiments and especially for multiple experiments carried out over days or weeks. By maintaining a fixed temperature and depth of anesthesia, any changes in the image data can be related to the experimental intervention rather than the experimental conditions during the imaging session.

Once the animal 10 is positioned on the bed 20, it is a simple matter to place the bed 20 in the chamber 30, 32, reattach the gas delivery line 46 from the nose cone 22 to the chamber 30, 32, and replace the top half of the chamber 32. The top half of the chamber 32 in this embodiment is specifically designed to fit closely, with an endplate 72 on one end that has a groove 36 to accept the lower portion of the chamber 30. The snug fit is further enhanced by a small O ring 24 that provides a small amount of pressure to the bed 20, as described above, to ensure the bed 20 is always in substantially the same location. The staging process of securing the animal 10 in this embodiment only takes a few minutes and typically is done just prior to the imaging session.

For research with multiple animals using the same protocol and/or radioisotopes, several animals (not shown) can be prepared at once and held until ready for imaging. For experiments using multiple imaging modalities, it is easy to move the animals between systems and have the next animal prepared and waiting in a chamber 30, 32 to go into the next available imaging session to make maximal and efficient use of the imaging systems.

Since the use of immunocompromised animals is commonplace, parts coming into contact with the animals can be sterilized. This embodiment of the chamber 30, 32 is designed in such a way that animals only come into contact with the bed 20. The bed 20 can easily be sterilized using various commercially available solutions or gas. Although, in this embodiment, the animal 10 does not come into contact with the chamber walls, the entire chamber 30, 32 can also be sterilized if desired.

By maintaining a constant flow of anesthetic gas, an even, reproducible level of anesthesia can easily be maintained. The anesthetic gas also produces a positive pressure within the chamber 30, 32, therefore preventing pathogens from entering.

The gas exits through the tube 44 in the back of the chamber 30, 32, which serves two purposes. First, since the gas is delivered at the nose of the animal 10, and vented at the other end of the chamber 30, 32, the whole chamber 30, 32 is filled with the anesthetic agent, ensuring complete anesthesia, even if the animal is not well placed into the nose cone 22. Second, the tube 44 for the exhaust has a Luer fitting for connection to the chamber, so the anesthetic agent can either be captured in an exhaust chamber (not shown) or vented. The pathogen barrier of the chamber 30, 32 permits in-vivo imaging of these animals using systems placed outside of barrier facilities and significantly expands the possible sites for installation and use. This reduces the expense related to barrier facilities, and increases the ease and speed of imaging studies.

The heating element 38 is controlled by the electronic systems 48 and does not require adjustment or monitoring by the investigator. Since imaging experiments are typically complicated and have many details requiring attention, the ability to plug in the heater 38 and no longer worry about the temperature is advantageous.

The invention has been described and illustrated by exemplary and preferred embodiments, but is not limited thereto. Persons skilled in the art will appreciate that a variety of modifications can be made without departing from the scope of the invention, which is limited only by the appended claims and equivalents thereof.

What is claimed is:

1. A method of in-vivo imaging of an animal, comprising:
   providing an animal having limbs;
   providing a first mounting surface;
   providing a bed removably secured to the mounting surface, sized to support the animal and coupled to a plurality of straps;
   placing the animal on the bed between the plurality of straps;
   tightening at least two of the plurality of straps around at least two of the limbs such that the animal is substantially secured in place relative to the bed;
   providing a first imaging device having an associated second mounting surface;
   fixing the first mounting surface to the second mounting surface;
   locating the bed and the animal within a field of view of the first imaging device;
   enclosing the animal in a chamber such that the animal is environmentally isolated from the second mounting surface, the chamber being fixed relative to or integral with the first mounting surface; and imaging the animal with the first imaging device to create a first image.

2. The method of claim 1, further comprising introducing gas anesthesia into the chamber.

3. A method of in-vivo imaging of an animal, comprising:
providing an animal having limbs;
providing a first mounting surface;
providing a bed integral with the mounting surface, sized to support the animal and coupled to a plurality of straps;
placing the animal on the bed between the plurality of straps;
tightening at least two of the plurality of straps around at least two of the limbs such that the animal is substantially secured in place relative to the bed;
providing a first imaging device having an associated second mounting surface;
fixing the first mounting surface to the second mounting surface;
locating the bed and the animal within a field of view of the first imaging device;
enclosing the animal in a chamber such that the animal is environmentally isolated from the second mounting surface, the chamber being fixed relative to or integral with the first mounting surface; and
imaging the animal with the first imaging device to create a first image.

4. The method of claim 3, further comprising introducing gas anesthesia into the chamber.

* * * * *